(12) United States Patent
Tao et al.

(10) Patent No.: US 10,398,528 B2
(45) Date of Patent: Sep. 3, 2019

(54) MEDICAL PENDANT ARM SYSTEM AND ROTATION SHAFT USED FOR THE SAME

(71) Applicant: MAQUET (SUZHOU) CO., LTD., Suzhou (CN)

(72) Inventors: Xiaowang Tao, Suzhou (CN); Qunhua Li, Suzhou (CN); Ming Ji, Suzhou (CN)

(73) Assignee: MAQUET (SUZHOU) CO., LTD., Suzhou (CN)

( * ) Notice: Subject to any disclaimer, the term of this patent is extended or adjusted under 35 U.S.C. 154(b) by 421 days.

(21) Appl. No.: 15/343,384

(22) Filed: Nov. 4, 2016

(65) Prior Publication Data

US 2017/0079743 A1    Mar. 23, 2017

Related U.S. Application Data

(63) Continuation of application No. PCT/CN2014/083522, filed on Aug. 1, 2014.

(30) Foreign Application Priority Data

May 6, 2014  (CN) .......................... 2014 1 0187994

(51) Int. Cl.
*A61B 90/50* (2016.01)
*F16M 11/08* (2006.01)
(Continued)

(52) U.S. Cl.
CPC ............. *A61B 90/50* (2016.02); *A61B 90/00* (2016.02); *F16C 19/16* (2013.01); *F16M 11/08* (2013.01);
(Continued)

(58) Field of Classification Search
CPC .... A61B 9/00; A61B 9/35; A61B 9/50; A61B 2090/508; F16C 19/16; F16M 11/08;
(Continued)

(56) References Cited

U.S. PATENT DOCUMENTS 6,095,468 A    8/2000  Chirico et al.
7,575,389 B2 *  8/2009  Nance ................. E05B 47/0038
                                                    403/109.2
(Continued)

FOREIGN PATENT DOCUMENTS

CN    201844175 U    5/2011
CN    102182759 A    9/2011
(Continued)

OTHER PUBLICATIONS

Translation of CN 102312946. Bei, et al. Jan. 11, 2012. Electromagnetic braking device for medical tower crane joint. (Year: 2012).*

(Continued)

*Primary Examiner* — Josh Skroupa
(74) *Attorney, Agent, or Firm* — Quarles & Brady LLP

(57) ABSTRACT

A medical pendant assembly has an anchor plate that is attachable to a roof structure and a first rotation shaft that includes a shaft outer ring, a shaft inner ring, and a ball spacer sleeve. The ball spacer sleeve is disposed between the shaft outer ring and the shaft inner ring. A lower portion of the shaft outer ring includes a first flange. An upper portion of the shaft outer ring includes a second flange. The second flange of the first rotation shaft is either attached directly to the anchor plate or attached to the anchor plate via an extension assembly. A first arm is attached to the first flange of the first rotation shaft.

4 Claims, 6 Drawing Sheets

(51) Int. Cl.
    *F16M 13/02* (2006.01)
    *F16C 19/16* (2006.01)
    *A61B 90/00* (2016.01)
    *F16M 11/20* (2006.01)
(52) U.S. Cl.
    CPC ........ *F16M 11/2014* (2013.01); *F16M 13/02* (2013.01); *F16M 13/027* (2013.01); *A61B 2090/508* (2016.02); *F16M 2200/022* (2013.01); *F16M 2200/066* (2013.01); *Y10T 403/32081* (2015.01)
(58) Field of Classification Search
    CPC .. F16M 11/2014; F16M 13/02; F16M 13/027; F16M 2200/022; F16M 2200/066; F16M 2200/068; Y10T 403/32016; Y10T 403/32081; Y10T 403/32262; Y10T 403/32591; Y10T 403/32606; Y10T 403/32975
    USPC ........................ 403/54, 62, 84, 117, 119, 164
    See application file for complete search history.

(56) References Cited

U.S. PATENT DOCUMENTS

| | | | |
|---|---|---|---|
| 7,770,860 | B1 | 8/2010 | Culpepper et al. |
| 8,376,095 | B2* | 2/2013 | Nuissl ............... F16C 19/30 188/171 |
| 8,979,097 | B2* | 3/2015 | Cole ............... F16C 19/16 280/14.24 |
| 9,551,458 | B2* | 1/2017 | Knappe ............ F16M 11/2014 |
| 9,605,800 | B2* | 3/2017 | Huang ............ F16M 11/2014 |
| 2004/0104328 | A1 | 6/2004 | Frick |
| 2005/0282673 | A1 | 12/2005 | Knappe et al. |
| 2010/0104234 | A1 | 4/2010 | Nuissl et al. |
| 2014/0086666 | A1* | 3/2014 | Grziwok ............ F16M 11/14 403/56 |

FOREIGN PATENT DOCUMENTS

| | | |
|---|---|---|
| CN | 102312946 A | 1/2012 |
| CN | 202211748 U | 5/2012 |
| CN | 103353050 A | 10/2013 |
| CN | 103486415 A | 1/2014 |
| CN | 203442447 U | 2/2014 |
| CN | 103953837 A | 7/2014 |
| CN | 203880364 U | 10/2014 |
| DE | 202013001995 U1 | 5/2013 |
| EP | 1473473 A1 | 11/2004 |
| GB | 724513 A | 2/1955 |
| JP | H07418 A | 1/1995 |
| JP | H0712641 A | 3/1995 |
| JP | 2002-510026 A | 4/2002 |
| JP | 2007-037270 A | 2/2007 |
| WO | 99/50587 A1 | 10/1999 |

OTHER PUBLICATIONS

International Search Report dated Jan. 28, 2015, issued during International Patent Application No. PCT/CN2014/083522, 3 pages.
Written Opinion for SG11201607069V, which corresponds to this application, dated Jun. 22, 2017, 8 pages.
Search Report for SG11201607069V, which corresponds to this application, dated May 25, 2017, 3 pages.
Japanese Office Action dated Mar. 19, 2018, issued for corresponding Japanese Patent Application No. 2016-555337 along with English translation, 4 pages.
Japanese Office Action (with English translation) dated Oct. 6, 2017, issued for corresponding Japanese patent application No. 2016-555337, 8 pages.
Extended European Search Report dated Dec. 4, 2017, issued for corresponding EP patent application No. 14891475.7, 9 pages.

* cited by examiner

MEDICAL PENDANT ARM SYSTEM AND ROTATION SHAFT USED FOR THE SAME

CROSS REFERENCE TO RELATED APPLICATIONS

The present application is a continuation-in-part filed under 35 U.S.C. § 111(a), and claims the benefit under 35 U.S.C. §§ 365(c) and 371 of PCT International Application No. PCT/CN2014/083522, filed Aug. 1, 2014, and which designates the United States of America, and Chinese Patent Application No. 201410187994.2, filed May 6, 2014. The disclosures of these applications are herein incorporated by reference in their entirety.

TECHNICAL FIELD

The present invention relates to the technical field of medical equipment, and more particularly, for example, to a medical pendant arm system and rotation shaft used for the same.

BACKGROUND

Medical pendant systems are medical equipment used in modern hospital operating rooms, intensive care units and the like. A medical pendant arm system is a component of a medical pendant.

Conventional medical pendant arm systems mainly have the following shortcomings: non-compact overall structure, complicated assembly and long assembly time, relatively more parts, and relatively difficult installation of electromagnetic brakes.

SUMMARY OF THE DISCLOSURE

One of the purposes of the present disclosure is to overcome the above-mentioned disadvantages of existing medical pendant arm systems by providing a medical pendant arm system that has a compact overall structure, simple assembly and short assembly time, and relatively less parts, and an electromagnetic brake or an air-bag brake that can be selectively installed.

In at least some exemplary embodiments, a medical pendant arm system may comprise an anchor plate, wherein the anchor plate is used for fixing to the roof structure in the installation space of the medical pendant arm system. The system may also comprise a first rotation shaft, wherein the first rotation shaft comprises a shaft outer ring, a shaft inner ring and a ball spacer sleeve. The ball spacer sleeve may be disposed between the shaft outer ring and the shaft inner ring, the lower portion of the shaft outer ring forming a rectangular flange, the upper portion of the shaft outer ring forming a circular flange, wherein the circular flange of the first rotation shaft is fixed directly to the anchor plate or fixed to the anchor plate via an extension column. The system may also comprise a first arm, wherein the first arm, in the vicinity of one end portion thereof, may be fixed to the rectangular flange of the first rotation shaft.

In at least some exemplary embodiments, the disclosed medical pendant arm system can have the following technical effects: compact overall structure, simple assembly and short assembly time, relatively less parts, and an electromagnetic brake or an air-bag brake that can be selectively installed.

In at least some exemplary embodiments, the disclosed medical pendant arm system may comprise a second rotation shaft, wherein the second rotation shaft may comprise a shaft outer ring, a shaft inner ring and a ball spacer sleeve. The ball spacer sleeve may be disposed between the shaft outer ring and the shaft inner ring, the lower portion of the shaft outer ring forming a rectangular flange, the upper portion of the shaft outer ring forming a circular flange, wherein the circular flange of the second rotation shaft may be fixed in the vicinity of the other end portion of the first arm. The system may also comprise a second arm, wherein the second arm, in the vicinity of one end portion thereof, may be fixed to the rectangular flange of the second rotation shaft.

In at least some exemplary embodiments, the medical pendant arm system can have the following technical effects: a dual arm system having compact overall structure may be constituted with simple assembly and short assembly time, relatively less parts, and an electromagnetic brake or an air-bag brake that can be selectively installed.

In at least some exemplary embodiments, the first rotation shaft and the second rotation shaft may be identical rotation shafts.

In at least some exemplary embodiments, the medical pendant arm system can have the following technical effects: modular design can be realized and its rotation shafts can be replaced, which may save production costs and replacement costs.

In at least some exemplary embodiments, the end portions of the first arm or the second arm may be downward bevelled.

In at least some exemplary embodiments, the medical pendant arm system can have the following technical effects: the space occupancy of the medical pendant arm system may be further reduced and the overall structural compactness may be increased.

In at least some exemplary embodiments, the rectangular flange of the first rotation shaft or the rectangular flange of the second rotation shaft can be used for installing an electromagnetic brake or an air-bag brake.

In at least some exemplary embodiments, the medical pendant arm system can have the following technical effect: an electromagnetic brake or an air-bag brake can be selectively installed (for example, involving little or substantially no change for the structure of the rotation shafts).

In at least some exemplary embodiments, the medical pendant arm system may also comprise a rotation shaft cover provided outside the first rotation shaft or the second rotation shaft, and the rotation shaft cover may be provided with a circular groove set between an upper rotation shaft cover and a lower rotation shaft cover thereof (e.g., the circular groove may be used for installing a circular brake indicator lamp).

In at least some exemplary embodiments, the medical pendant arm system can have the following technical effect: a circular brake indicator lamp can be installed at an appropriate position to (e.g., explicitly) make a lamplight indication when a brake of a certain rotation shaft releases.

In at least some exemplary embodiments, the first rotation shaft or the second rotation shaft may also comprise a mechanical brake, and the periphery of the mechanical brake may have threads for being screwed into the threaded hole of the rectangular flange of the first rotation shaft or the rectangular flange of the second rotation shaft.

In at least some exemplary embodiments, the medical pendant arm system can have the following technical effect: a mechanical brake can be installed in a simple and effective manner to increase damping torque.

In at least some exemplary embodiments, the medical pendant arm system may comprise an upper lining board and a lower lining board respectively provided at the upper end and the lower end of the first rotation shaft or the second rotation shaft.

In at least some exemplary embodiments, the medical pendant arm system can have the following technical effect: the contact stress at the junction of the rotation shaft and the arm may be reduced.

In at least some exemplary embodiments, the upper surface of the first arm or the second arm may be provided with an opening.

In at least some exemplary embodiments, the medical pendant arm system can have the following technical effects: on one aspect, it can facilitate the assembly of the gas pipes and lines, and on the other aspect, a top ambient illumination LED lamp can be selectively installed according to the requirements of customers.

In at least some exemplary embodiments, the first rotation shaft or the second rotation shaft may also comprise a limit column and a limit block set outside the upper portion thereof.

In at least some exemplary embodiments, the medical pendant arm system can have the following technical effect: the rotation range of the rotation shaft can be effectively limited.

In at least some exemplary embodiments, when the circular flange of the first rotation shaft is fixed to the anchor plate by the extension column, the extension column may be composed of a cylindrical member having multiple extension column bores distributed along its circumference.

In at least some exemplary embodiments, the medical pendant arm system can have the following technical effects: the extension column cover provided outside the extension column can be omitted, and the number of components may be reduced so that good appearance and the cleanliness of the medical pendant arm system may be provided.

In at least some exemplary embodiments, the mechanical brake may comprise a threaded portion located outside when installed, a friction head located inside when installed, and a disc spring located between the threaded portion and the friction head.

In at least some exemplary embodiments, the medical pendant arm system can have the following technical effect: a suitable mode for a mechanical brake is provided, so that the damping torque can be increased in a simple and effective manner.

In at least some exemplary embodiments, a rotation shaft may be used for a medical pendant arm system, the rotation shaft comprising a shaft outer ring, a shaft inner ring and a ball spacer sleeve, the ball spacer sleeve being disposed between the shaft outer ring and the shaft inner ring, the lower portion of the shaft outer ring forming a rectangular flange, and the upper portion of the shaft outer ring forming a circular flange.

In at least some exemplary embodiments, the rotation shaft used for the medical pendant arm system can have the following technical effects: the overall structure of the entire medical pendant arm system may be compact, with relatively simple assembly and short assembly time, and relatively less parts, and an electromagnetic brake or an air-bag brake can be selectively installed.

DETAILED DESCRIPTION AND INDUSTRIAL APPLICABILITY

The present disclosure is further described in connection with drawings and exemplary embodiments as follows and elaborated in more detail in the following description in order to fully understand the present disclosure, but it is evident that the present disclosure can be implemented in many other ways which are different from those described herein; generalization and deduction can be made by a skilled in the art without departing from the connotation of the disclosure according to practical application, and therefore the protective scope of the present disclosure should not be limited by the specific content of embodiments of the present disclosure herein.

Figure 1:
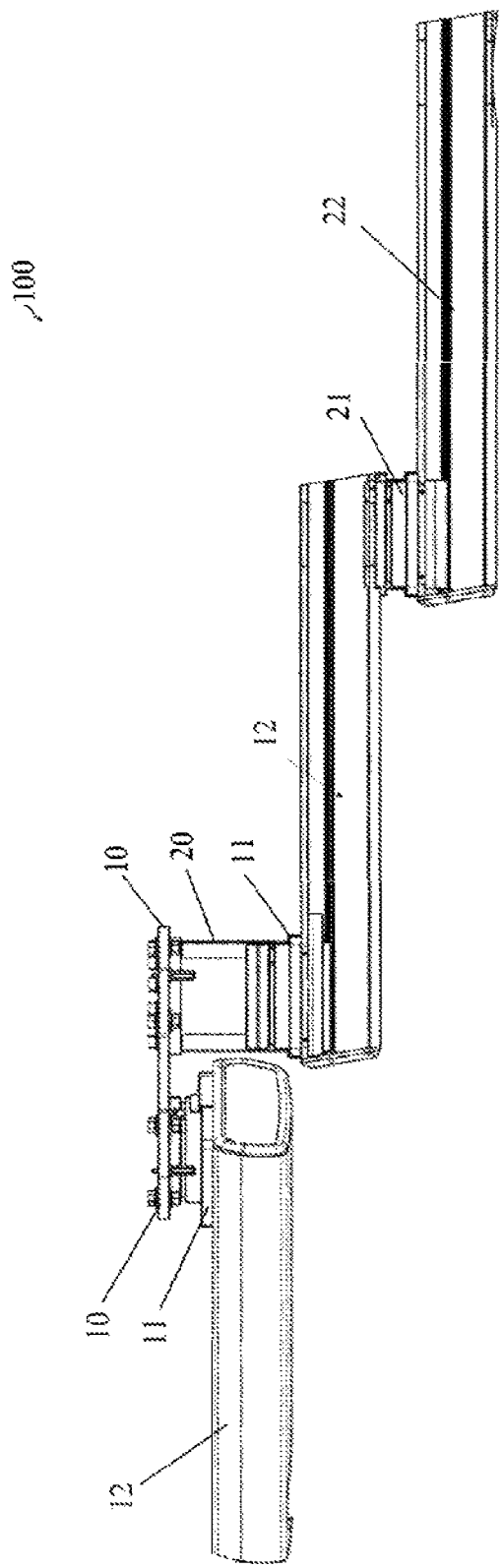
FIG. 1 shows the front view for the exemplary medical pendant arm system.
Figure 2:
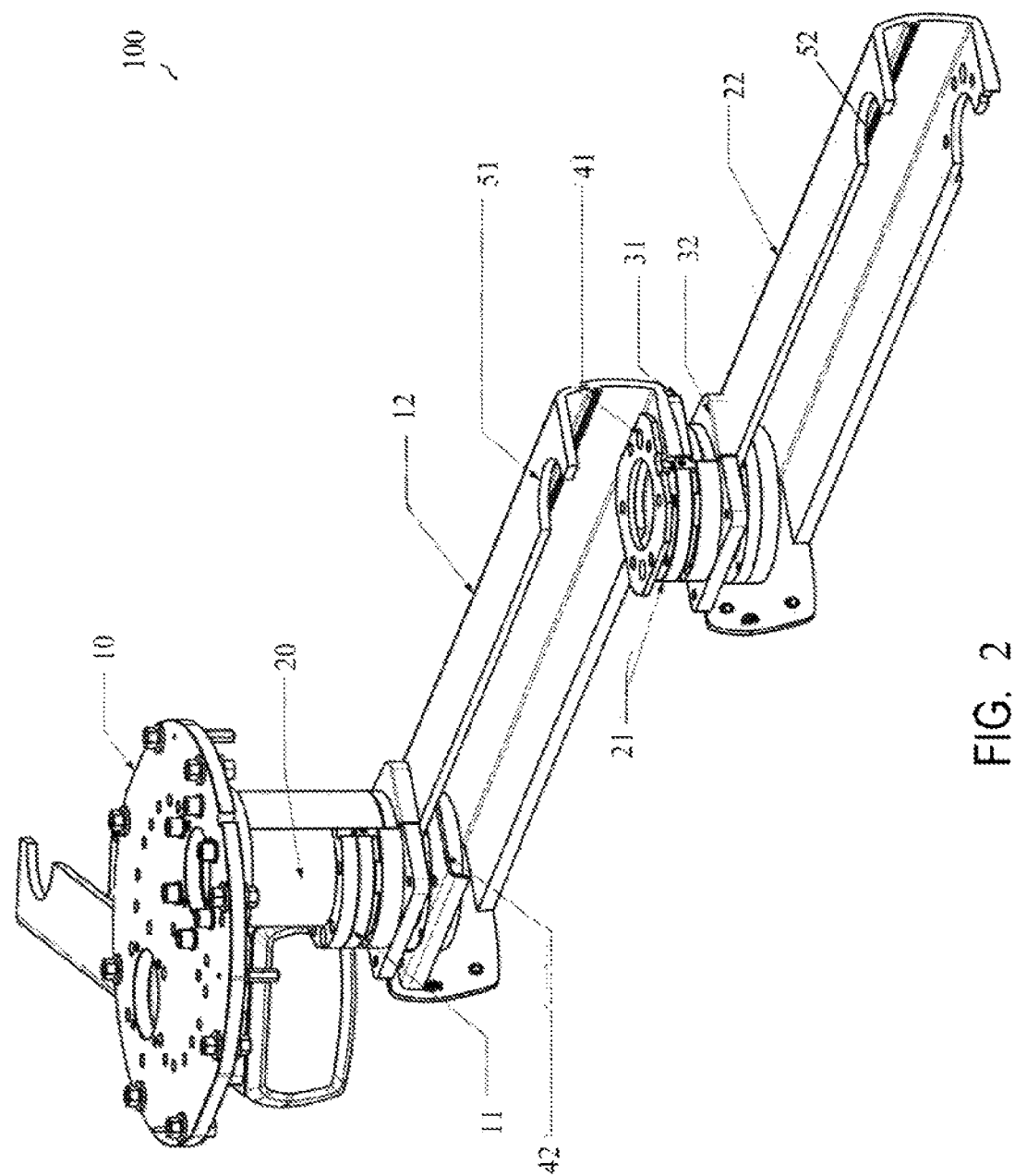
FIG. 2 shows the partially cutaway three-dimensional view for the exemplary medical pendant arm system.
Figure 3:
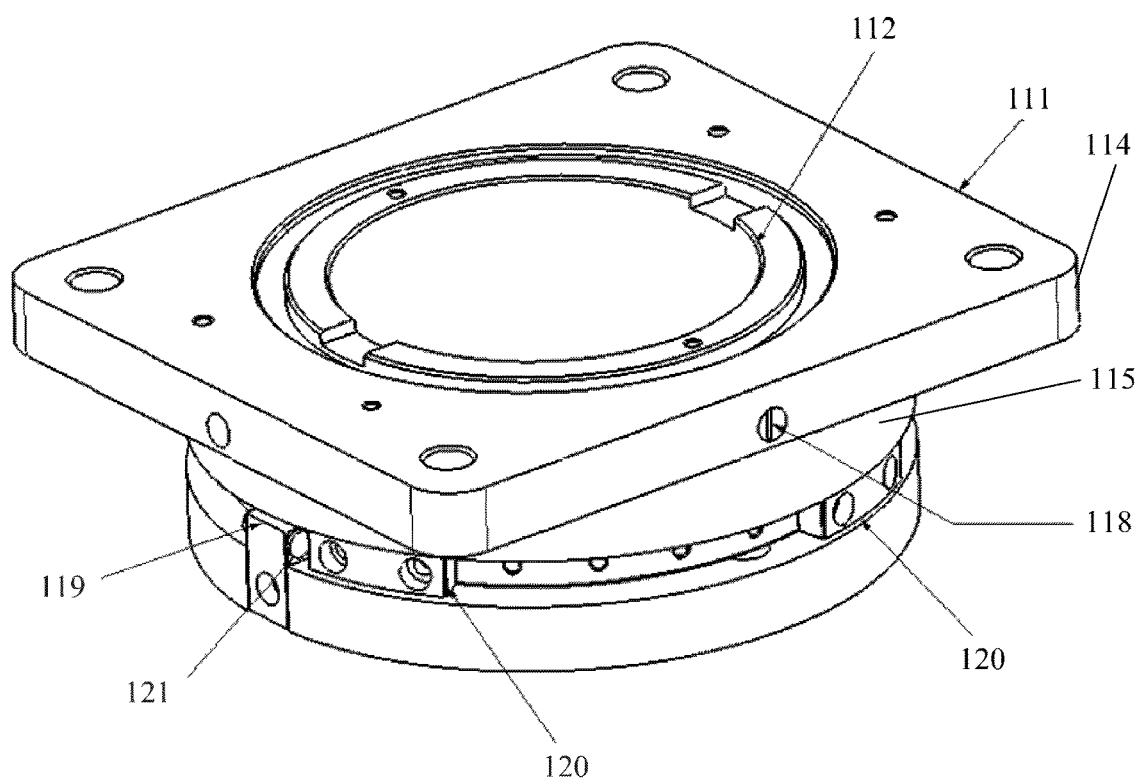
FIG. 3 shows the three-dimensional view for the rotation shaft used for the exemplary medical pendant arm system, in which the upper and lower relationship of the rotation shaft may be reversed (e.g., in contrast to the upper and lower relationship when it may be installed in the medical pendant arm system) for clarity.
Figure 4:
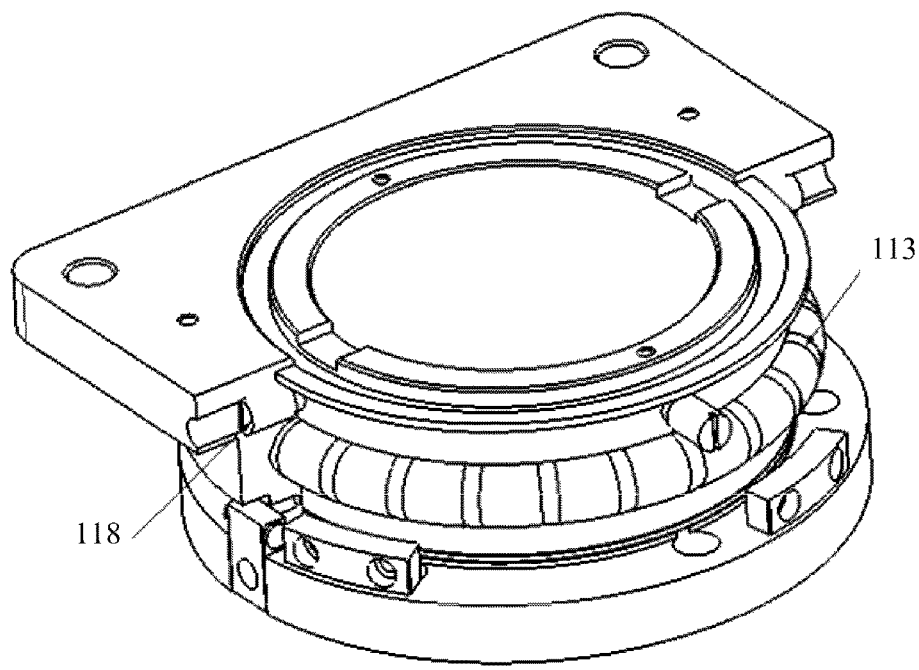
FIG. 4 shows the partially cutaway three-dimensional view for the rotation shaft used for the exemplary medical pendant arm system, in which the upper and lower relationship of the rotation shaft is reversed for clarity.
Figure 5:
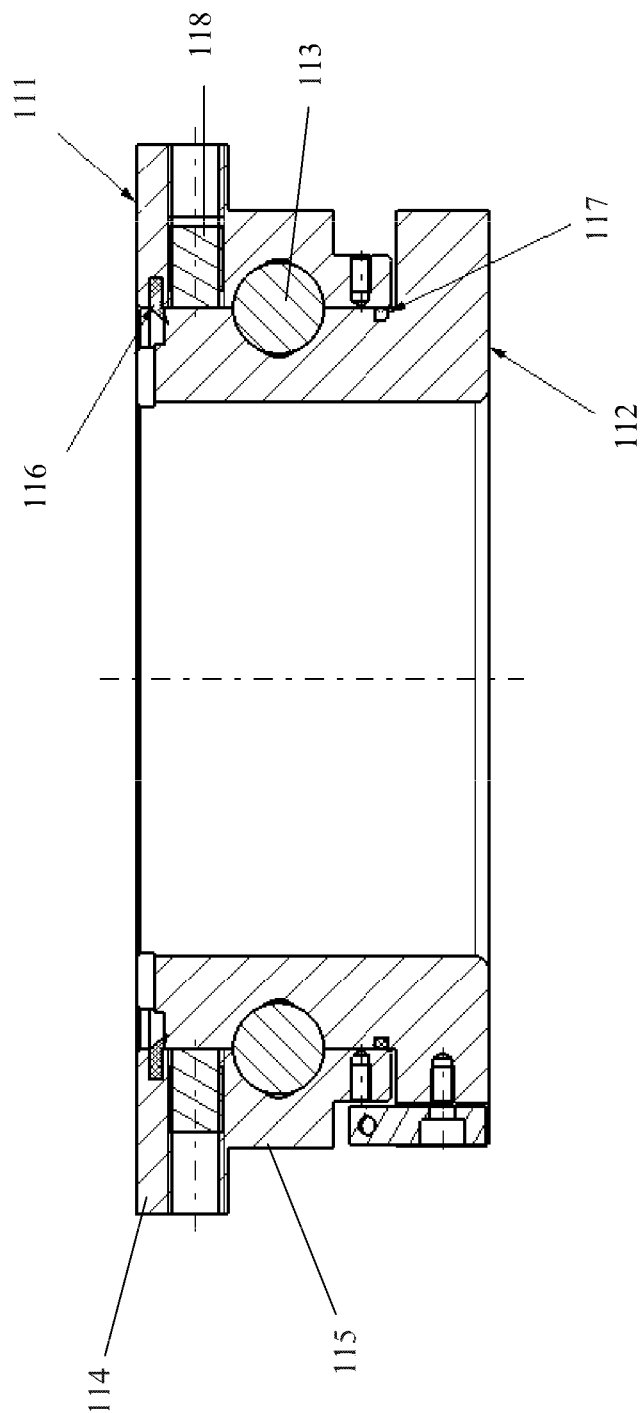
FIG. 5 shows the section view for the rotation shaft used for the exemplary medical pendant arm system, in which the upper and lower relationship of the rotation shaft is reversed for clarity.

FIG. 1 shows the front view for the exemplary medical pendant assembly (e.g., medical pendant arm system 100). FIG. 2 shows the partially cutaway three-dimensional view for the medical pendant arm system 100. FIG. 3 shows the three-dimensional view for the rotation shafts 11 and 21 used for the medical pendant arm system 100, in which the upper and lower relationship of the rotation shaft is reversed (e.g., in contrast to the upper and lower relationship when it is installed in the medical pendant arm system 100) for clarity. FIG. 4 shows the partially cutaway three-dimensional view for the rotation shafts 11 and 21 used for the medical pendant arm system 100, in which the upper and lower relationship of the rotation shaft is reversed for clarity. FIG. 5 shows the section view for the rotation shafts 11 and 21 used for the medical pendant arm system 100, in which the upper and lower relationship of the rotation shaft is reversed for clarity.

The medical pendant arm system 100 of the present invention may comprise an anchor plate 10, wherein the anchor plate 10 may be used for attaching (e.g., fixing, attachable, and/or fixable) to the roof structure in the installation space of the medical pendant arm system. The top structure may, for example, include the ceilings of an operating room and an intensive care unit in a hospital. A first rotation shaft 11 may be provided, wherein the first rotation shaft 11 may comprise a shaft outer ring 111, a shaft inner ring 112 and a ball spacer sleeve 113, the ball spacer sleeve 113 being provided between the shaft outer ring 111 and the shaft inner ring 112, the lower portion of the shaft outer ring 111 forming a first flange of any suitable shape (e.g., a rectangular flange 114), the upper portion of the shaft outer ring 111 forming a second flange of any suitable shape (e.g., a circular flange 115), wherein the circular flange 115 of the first rotation shaft 11 may be fixed directly to the anchor plate 10 or fixed to the anchor plate 10 via (e.g., by) an extension assembly (e.g., extension column 20). A first arm 12 may be provided, wherein the first arm 12, in the vicinity of one end portion thereof, may be fixed to the rectangular flange 114 of the first rotation shaft 11.

The upper circular flange 115 of the rotation shaft 11 may be formed integrally with the lower rectangular flange 114.

The exemplary medical pendant arm system can involve modular design, have a compact overall structure, be easy to assemble with a short assembly time, and can have relatively less parts, and an electromagnetic brake or an air-bag brake can be selectively installed.

Note that, "upper", "lower", "front", "rear", "left", "right" and the like used herein are only exemplary directions defined to facilitate the description of the invention. For example, as shown in FIG. 1, the direction of the top side in the paper is "upper", and the direction of the bottom side in the paper is "lower", however, as shown in FIG. 5, the upper and lower relationship is reversed for clarity, that is, the direction of the top side in the paper is "lower", and the direction of the bottom side in the paper is "upper". Of course, those skilled in the art on the basis of the present invention can understood that "upper", "lower", "front", "rear", "left", "right" and other directions can also be defined in other ways, which also fall into the protective scope of the present disclosure.

In at least some exemplary embodiments, the medical pendant arm system 100 may comprise a second rotation shaft 21, wherein the second rotation shaft may comprise a shaft outer ring 111, a shaft inner ring 112 and a ball spacer sleeve 113, the ball spacer sleeve 113 being provided between the shaft outer ring 111 and the shaft inner ring 112, the lower portion of the shaft outer ring 111 forming a rectangular flange 114. The upper portion of the shaft outer ring 111 may form a circular flange 115, wherein the circular flange 115 of the second rotation shaft 21 may be fixed in the vicinity of the other end portion of the first arm 12. A second arm 22 may be provided, wherein the second arm 22, in the vicinity of one end portion thereof, may be fixed to the rectangular flange 114 of the second rotation shaft 21.

Accordingly, in at least some exemplary embodiments, a dual-arm system having compact overall structure may be constituted. For example, the distance between the arms may be effectively shortened, with simple assembly and short assembly time, and relatively less parts, and an electromagnetic brake or an air-bag brake can be selectively installed.

In at least some exemplary embodiments, the first rotation shaft 11 and the second rotation shaft 21 may be substantially identical rotation shafts. Furthermore, the first arm 12 and the second arm 22 may be identical arms.

In at least some exemplary embodiments, the medical pendant arm system can involve (e.g., realize) modular design and its main components (e.g., rotation shafts and/or arms) can be replaced (e.g., replace each other), which may save production costs and replacement costs.

In at least some exemplary embodiments, in addition to one rotation shaft and one arm or two rotation shafts and two arms, three or more rotation shafts and three or more arms can also be used.

In at least some exemplary embodiments, a dual pendant may be provided. The circular flange of the rotation shaft 11 of one of the medical pendants (e.g., the medical pendant on the left in FIG. 1) may be directly connected and fixed to the anchor plate 10, in the other medical pendant (e.g., the medical pendant on the right in FIG. 1). In order to avoid mutual interference, an extension column 20 may be provided (e.g., installed) on the circular flange of the rotation shaft 11. The circular flange of the rotation shaft 11 of the medical pendant on the right in FIG. 1 may be fixed to the anchor plate 10 by the extension column 20.

In at least some exemplary embodiments, in order to provide for suitable height or size of the extension column 20 (e.g., being suitably small), the end portion of the arms 12 and 22 may be downward bevelled. Accordingly, the space occupancy of the medical pendant arm system can be further reduced and the overall structural compactness may be increased.

In at least some exemplary embodiments, in order to provide for the center distance between the rotation shafts 11 and 11 of the two medical pendants being less than 300 mm, the rotation shafts may be designed into a layout so that the circular flange may be at the top and the rectangular flange may be at the bottom (e.g., the lower portion of the shaft outer ring may form the rectangular flange, and the upper portion of the shaft outer ring may form the circular flange). In this way, not only the center distance between the rotation shafts of the two medical pendants can be shortened, but also the appearance of the extension column cover can be suitable (e.g., perceived as concise and elegant by an observer).

The lower rectangular flanges of the rotation shafts 11 and 21 may be designed into a rectangular shape, the purpose of which may be to install an electromagnetic brake (for example, of 120 Nm brake torque) at the lower ends of the rotation shafts 11 and 21, or to install an air-bag brake (for example, involving little or substantially no change of structure of the rotation shafts according to the request of customers). For example, a brake may be disposed at a flange (e.g., the lower rectangular flanges of the rotation shafts 11 and 21). That is to say, for example, the rectangular flanges of the rotation shafts can be used for installing an electromagnetic brake or an air-bag brake. For example, a snap port for the electromagnetic brake and a backing board-fixing hole for the air-bag brake can be provided on the shaft inner ring 111, and an electromagnetic brake-fixing hole or an air-bag brake-fixing hole can be provided on the shaft outer ring 112.

In at least some exemplary embodiments, the medical pendant arm system may also comprise rotation shaft covers 31 and 32 provided outside the rotation shafts 11 and 21. The rotation shaft covers may be provided with a circular groove set between the upper rotation shaft cover 31 and the lower rotation shaft cover 32 thereof, the circular groove being used for installing a circular brake indicator lamp. The circular brake indicator lamp may light up when a brake of the rotation shafts 11 and 21 releases.

In at least some exemplary embodiments, the end covers of the arms 12 and 22 may be composed of two portions: the end cover housing and the end cover-fixing board. For example, when the end covers are installed, the end cover-fixing board may be firstly fixed by several (e.g., two) screws and several threaded holes inside the arms 12 and 22. Then, for example, the end cover housing may be directly pushed into the corresponding hole in the end cover-fixing board. In this way, the time for the assembly and disassembly of the arm end covers may be shortened, and the complexity for the installation may be reduced.

In at least some exemplary embodiments, as shown in FIGS. 3-5, the rotation shafts 11 and 21 may comprise a mechanical brake 118, the periphery of the mechanical brake 118 having threads that are screwed into the threaded hole of the rectangular flange 114 of the rotation shafts 11 and 21. The number of mechanical brakes 118 can be increased according to the space, thus increasing the damping torque. For example, in the examples shown in FIGS. 3-5, four mechanical brakes 118 may be employed.

In at least some exemplary embodiments, in order to reduce the contact stress at the junction between the rotation shafts 11 and 21 and the arms 12 and 22 (aluminium section in general) and increase the connecting strength, the medical pendant arm system may also comprise an upper lining board 41 and a lower lining board 42 disposed at the upper end and the lower end of the rotation shaft, respectively.

In at least some exemplary embodiments, the upper surfaces of the arms 12 and 22 are provided with openings 51 and 52. In this way, for example, this exemplary configuration can facilitate the assembly of the gas pipes and lines, and also a top ambient illumination LED lamp can be selectively installed according to request of customers.

In at least some exemplary embodiments, as shown in FIGS. 3-5, the first rotation shafts 11 and 21 may also comprise a limit column 119 and a limit block 120 set outside the upper portion thereof. For example, the upper circular flange of the rotation shaft 11 may be (e.g., totally) provided with 6 round holes that are uniformly distributed, but the rotation shaft 21 may only have 4 holes based on the overturning moment difference supported by them.

In at least some exemplary embodiments, as shown in FIG. 3, a cushion 121 may further be provided on the area of the limit column 119 to be contacted with the limit block 120.

In at least some exemplary embodiments, as shown in FIG. 5, the rotation shafts 11 and 21 may also comprise an upper sealing ring 117 and a lower sealing ring 116, the upper sealing ring 117 being disposed (e.g., provided) between an upper inside portion of the shaft outer ring 111 and an upper outside portion of the shaft inner ring 112, and the lower sealing ring 116 being disposed (e.g., provided) between a lower inside portion of the shaft outer ring 111 and a lower outside portion of the shaft inner ring 112.

In at least some exemplary embodiments, as shown in FIG. 2, when the circular flange 115 of the first rotation shaft 11 is fixed to the anchor plate 10 by the extension column 20, an extension column cover can be provided outside the extension column 20 (e.g., for the purpose of the good appearance and cleanliness of the medical pendant arm system).

Figure 6A:
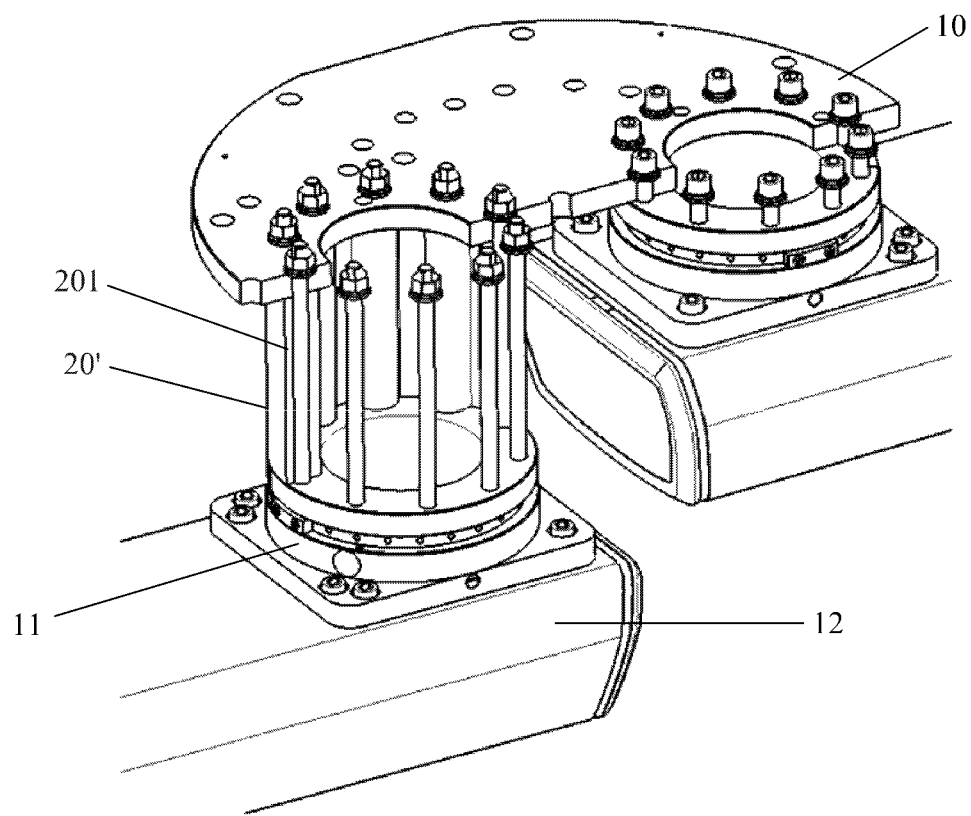
FIGS. 6(*a*) and 6(*b*) show another embodiment for the extension column used for the exemplary medical pendant arm system, in which FIG. 6(*a*) shows the partially cutaway schematic of the extension column when it is installed in the medical pendant arm system, and FIG. 6(*b*) separately shows the three-dimensional view for the extension column.
Figure 6B:
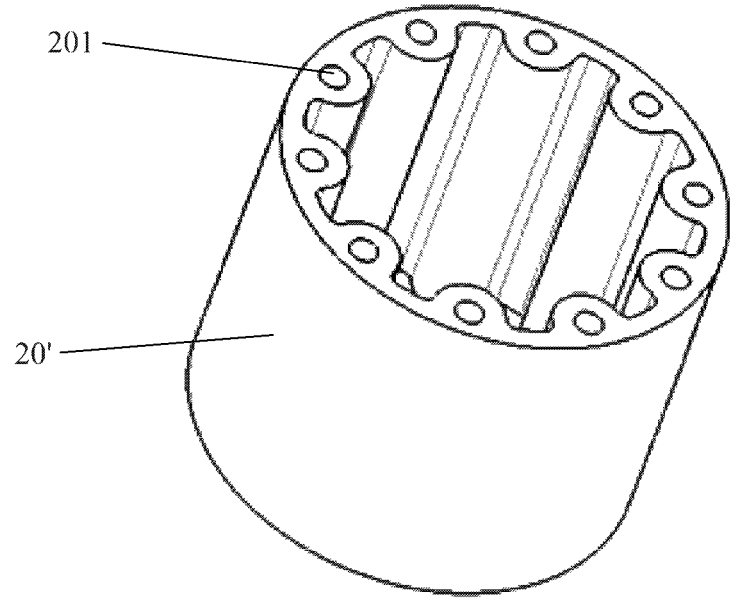

FIGS. 6(a) and 6(b) show another exemplary embodiment for the extension column used for the medical pendant arm system, in which FIG. 6(a) shows the partially cutaway schematic of the extension column when it is installed in the medical pendant arm system, and FIG. 6(b) separately shows the three-dimensional view for the extension column.

The extension column 20' may be composed of a cylindrical member having multiple extension column bores 201 distributed along its circumference. When the circular flange 115 of the first rotation shaft 11 is fixed to the anchor plate 10 by the extension column 20', multiple threaded rods may pass through multiple extension column bores 201, respectively, and their lower ends may be connected to the threaded holes located in the first rotation shaft 11, and their upper ends may pass through the unthreaded holes (non-threaded holes) in the anchor plate 10 and tightened via the nuts above the anchor plate 10. The extension column 20' can be subjected to outer surface spray coating. In this way, the extension column cover provided outside the extension column may be, for example, omitted.

Figure 7A:
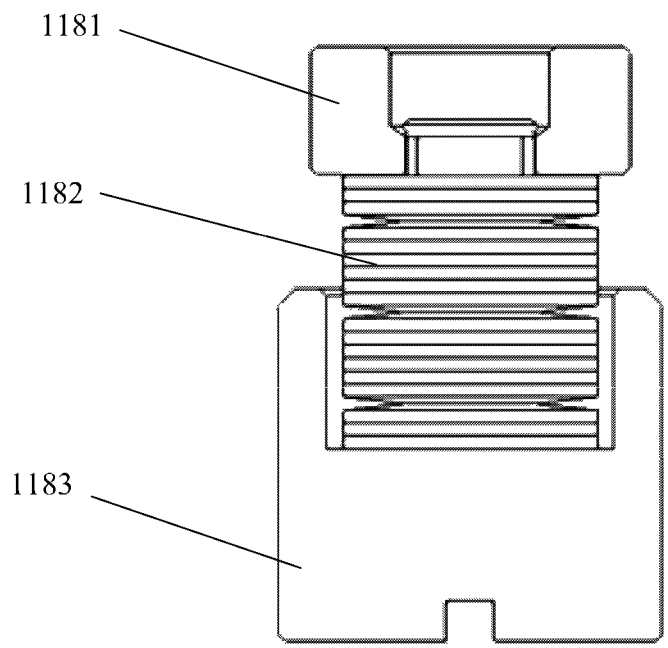
FIG. 7(*a*) shows the front view for the mechanical brake used for the exemplary medical pendant arm system, and FIG. 7(*b*) shows the three-dimensional view for the mechanical brake used for the medical pendant arm system.
Figure 7B:
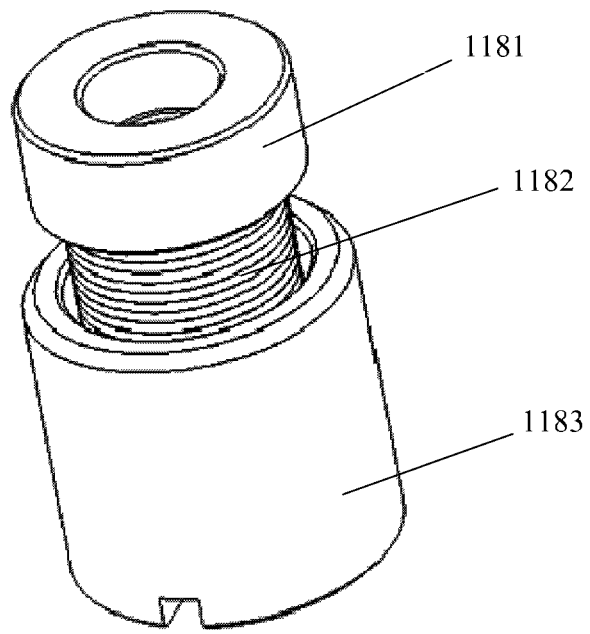

FIG. 7(a) shows the front view for the mechanical brake used for the medical pendant arm system, and FIG. 7(b) shows the three-dimensional view for the mechanical brake used for the medical pendant arm system.

The mechanical brake 118 may comprise a threaded portion 1183 located outside (e.g., the side away from the shaft inner ring) when it is installed (e.g., when it is installed in the rotation shaft), a friction head 1181 located inside (i.e., the side toward the shaft inner ring) when it is installed, and a disc spring 1182 located between the threaded portion 1183 and the friction head 1181. When the mechanical brake 118 is to be installed in the rotation shaft, a screwdriver can be used to screw the mechanical brake 118 into the rotation shaft. When a certain torque is achieved, the friction head 1181, which may be affected (e.g., deformed or pressed or impacted or "suffered") from the press of the disc spring 1182, may press tightly against the outer cylindrical surface of the shaft inner ring 111.

It will be apparent to those skilled in the art that various modifications and variations can be made to the disclosed method and apparatus. Other embodiments will be apparent to those skilled in the art from consideration of the specification and practice of the disclosed method and apparatus. It is intended that the specification and the disclosed examples be considered as exemplary only, with a true scope being indicated by the following claims.

What is claimed is:
1. A medical pendant assembly, comprising:
an anchor plate that is attachable to a roof structure; and
a rotation shaft that includes a shaft outer ring, a shaft inner ring, and a ball spacer sleeve;
wherein the ball spacer sleeve is disposed between the shaft outer ring and the shaft inner ring;
wherein a lower portion of the shaft outer ring includes a first flange;
wherein an upper portion of the shaft outer ring includes a second flange;
wherein the second flange of the rotation shaft is either attached directly to the anchor plate or attached to the anchor plate via an extension assembly;
wherein a first arm is attached to the first flange of the rotation shaft; and
wherein a brake is disposed at the first flange;
the medical pendant assembly further comprising a rotation shaft cover disposed outside the rotation shaft, the rotation shaft cover including an upper rotation shaft cover, a lower rotation shaft cover, and a circular groove that is disposed between the upper rotation shaft cover and the lower rotation shaft cover; wherein the circular groove includes a brake indicator lamp.
2. The medical pendant assembly of claim 1, wherein the brake is an electromagnetic brake or an air-bag brake.
3. The medical pendant assembly of claim 1, wherein:
the brake is a mechanical brake; and
a periphery of the mechanical brake includes threads configured to be screwed into a threaded hole of the first flange.

4. The medical pendant assembly of claim 1, wherein:
the brake is a mechanical brake; and
the brake includes a threaded portion, a friction head, and a disc spring disposed between the threaded portion and the friction head.

\* \* \* \* \*